(12) United States Patent
Huatan et al.

(10) Patent No.: US 9,012,436 B2
(45) Date of Patent: Apr. 21, 2015

(54) LIPID COMPOSITION

(75) Inventors: Hiep Huatan, Maidstone (GB); Richard Ross, Sheffield (GB)

(73) Assignee: Diurnal Limited, Cardiff (GB)

( * ) Notice: Subject to any disclaimer, the term of this patent is extended or adjusted under 35 U.S.C. 154(b) by 495 days.

(21) Appl. No.: 12/989,948

(22) PCT Filed: Apr. 27, 2009

(86) PCT No.: PCT/GB2009/001068
§ 371 (c)(1),
(2), (4) Date: Oct. 27, 2010

(87) PCT Pub. No.: WO2009/133352
PCT Pub. Date: Nov. 5, 2009

(65) Prior Publication Data
US 2011/0039814 A1 Feb. 17, 2011

(30) Foreign Application Priority Data

Apr. 28, 2008 (GB) .................................. 0807605.1

(51) Int. Cl.
*A01N 47/00* (2006.01)
*A61K 31/21* (2006.01)
*A61K 9/48* (2006.01)
*A61K 31/568* (2006.01)
*A61K 9/107* (2006.01)

(52) U.S. Cl.
CPC ............. *A61K 9/4858* (2013.01); *A61K 9/1075* (2013.01); *A61K 31/568* (2013.01)

(58) Field of Classification Search
None
See application file for complete search history.

(56) References Cited

U.S. PATENT DOCUMENTS

| 4,098,802 A * | 7/1978 | van der Vies ................. 552/638 |
| 6,652,880 B1 * | 11/2003 | Aylwin et al. ................. 424/455 |
| 7,138,389 B2 * | 11/2006 | Amory et al. ................. 514/171 |
| 2005/0043285 A1 | 2/2005 | Evans et al. |
| 2005/0176692 A1 | 8/2005 | Amory et al. |

FOREIGN PATENT DOCUMENTS

| EP | 0 904 064 B1 | 10/2001 |
| EP | 1 743 646 A2 | 1/2007 |
| GB | 1 567 515 | 5/1980 |
| JP | 52-148060 A | 12/1977 |
| JP | 2003-526620 A | 9/2003 |
| JP | 2006-520377 A | 9/2006 |
| WO | WO 00/59482 A1 | 10/2000 |
| WO | WO 2004/080383 A2 | 9/2004 |

OTHER PUBLICATIONS

Kobayashi and Tsukamoto, "Hormonal Therapy for Young Elderly and Elderly (Particulars), Indication for Androgen Replacement Therapy," *Modern Physician* 27:1071-1074, 2007. (English Translation Only).

Tamai and Hori, Special Topic Sexual gland diseases—From bench to Bedside—"Medical Treatment of Hypogonadism," *Pediatric Practice* 65:1644-1648, 2002. (English Translation Only).

Amory and Bremner, "Oral Testosterone in Oil Plus Dutasteride in Men: A Pharmacokinetic Study," *J. Clin. Endocrinol.* 90:2610-2617, 2005.

* cited by examiner

*Primary Examiner* — Craig Ricci
*Assistant Examiner* — Jared D Barsky
(74) *Attorney, Agent, or Firm* — Klarquist Sparkman, LLP

(57) ABSTRACT

We describe lipid based pharmaceutical compositions adapted for oral delivery and optionally delivery in accordance with a circadian rhythm.

10 Claims, 2 Drawing Sheets

LIPID COMPOSITION

CROSS REFERENCE TO RELATED APPLICATIONS

This is the U.S. National Stage of International Application No. PCT/GB2009/001068, filed Apr. 27, 2009, which was published in English under PCT Article 21(2), which in turn claims the benefit of Great Britain Application No. 0807605.1, filed Apr. 28, 2008.

The invention relates to pharmaceutical compositions adapted for oral delivery and optionally delivery in accordance with a circadian rhythm; and including methods for the treatment of hormone related conditions that use the compositions.

Steroid hormones represent a large generic group of compounds that include adrenal steroids (aldosterone, cortisol, DHEA, DHEAS), thyroid hormone and retinoic acid, vitamin D and gonadal steroids (androstenedione, dihydrotestosterone, estradiol, progesterone and testosterone) that regulate male and female homeostasis and development. Two important groups of steroid hormone are the oestrogens and androgens. Oestrogens are female steroids that regulate the female oestrous cycle and are crucial in female reproduction and in the development of female secondary sexual characteristics. There are three types of oestrogen; oestradiol, estriol and estrone. The oestrogens are produced primarily by the ovaries in response to follicle stimulating hormone and luteinizing hormone. Oestrogens exert their effects via oestrogen receptors which initiate signal transduction cascades to regulate gene expression. An example of an androgen is testosterone. Testosterone is produced in the testes of males and the ovaries of females with small amounts secreted by the adrenal glands. In both males and females testosterone is a key steroid involved in regulating fertility, development, libido, body composition and energy metabolism. The androgens exert their effects through interaction with androgen receptors to regulate gene expression in target tissues. Testosterone can be produce in its natural form or as synthetic analogues that have better bioavailability when administered [e.g. either by alkylation or esterification of testosterone].

Diseases associated with excess or insufficient production of oestrogens or androgens are typically treated using hormone therapy. In addition, oestrogens and androgens are used as contraceptives. Hormone therapy includes the administration of hormone agonists or antagonists in the treatment of diseases. For example hormone therapy is used in the treatment of cancer typically by the administration of steroid hormones. Hormone replacement therapy is used to replace oestrogen and testosterone in pre-menopausal and post-menopausal women and also to replace hormones lost as a consequence of surgically induce menopause [e.g. hysterectomy or orchidectomy]. Oestrogen therapy is used in post menopausal women to treat or prevent osteoporosis and other symptoms of menopause. Oestrogens are also used in the treatment vaginal atrophy, amenorrhea and dysmenorrhea. Testosterone and testosterone analogues are used in the treatment of hypogonadism in males which results from little or no testosterone production by the testes. Other indications that use testosterone or analogues of testosterone include the treatment of fertility, lack of libido, osteoporosis, increase muscle growth, anaemia and depression.

Steroid hormone replacement therapy, in particular testosterone replacement therapy, is facilitated by a number formulations and routes of delivery. For example, most testosterone regimes involve the use of parenteral injections, skin patches, gels or buccal tablets because currently available oral forms of testosterone (either alkylated or esterified), present significant pharmacokinetic variability and long-term safety issues. Injections administered via intramuscular route every 1-3 weeks offer a solution to the pharmacokinetic variability issue however they are known to be painful and highly inconvenient to use. Testosterone undecanoate injections maybe given once every 10 to 12 weeks but do not provide any circadian variation and are painful. Testosterone patches (scrotal and non-scrotal) are generally preferred by patients but can cause moderate to severe skin reactions due to the vehicle that facilitates enhancement in the dermal absorption of testosterone. Testosterone gels are by far the most effective and widely used products. They are however, expensive and care must be taken to avoid inadvertent exposure to women and children. In addition many patients do not like applying the gel because of the quantity and inconvenience.

There is a need to develop alternative delivery means for the administration of steroid hormones, in particular native forms of steroid hormone such as testosterone. A preferred route of delivery is oral.

The delivery of steroids such as testosterone by oral means is known in the art. For example, WO2005/076899 discloses oral administration of testosterone in an oil vehicle in combination with finasteride or dutasteride to increase bioavailability. Finasteride and dutasteride are 5 alpha reductase inhibitors which inhibit the conversion of testosterone to a more active form dihydrotestosterone. EP0 001 851 discloses oral formulations of steroids in combination with tocol [a condensate of hydroquinone and phytol]. US2007/0026066 describes a complex delivery vehicle that provides for the sustained release of drugs, for example testosterone by combining the active agent in a lipid vehicle which is microencapsulated. Furthermore, Amory and Bremner [J. Clin Endocrinol Metab, 90(5), 2005, pp-2610-2617] demonstrate that delivery of testosterone in an oily vehicle (sesame oil) yielded efficacious serum levels. In WO2006/113505 a lipid based delivery vehicle is described that includes multiple lipid entities comprising hydrophilic and lipophilic functions that is adapted for the oral delivery of hydrophobic drugs such as testosterone and testosterone esters.

The main challenge with oral delivery of, for example testosterone, is that whilst the hormone undergoes rapid and complete absorption, there is considerable metabolism in both the gut wall and during first hepatic pass which accounts for almost 98% reduction in bioavailability. Attempts to deliver testosterone (in a crystalline powder form), up to doses around 200 mg, have largely been unsuccessful, resulting in very low level of exposure in serum. Manipulation of the crystalline form of testosterone has also had little effect on its bioavailability, as the principal hepatic metabolic pathway remains unchanged. As a result of the difficulty in avoiding the metabolic instability, efforts to improve the bioavailability of testosterone has been focused mainly on the development of more stable chemical adducts via either alkylation or esterification.

Lipid based formulations for oral drug delivery comprise either "simple" mono or binary oil mixtures, or more "elaborate" multi-component systems such as micelles, microemulsions, self-emulsifying systems, liposomes or macroemulsions. The utility of multiple component lipid based formulations are thought to improve drug solubilisation and increase the propensity for the formulation to undergo emulsification in vivo thus enabling rapid uptake into the lymphatic system. However recent studies have suggested that these assertions may not be correct as sufficient emulsification occurs in vivo without the need for additional exogenous emulsifying agents. Furthermore, the colloidal particle size ranges (which have been engineered to match those required for lymphatic uptake) are not generally replicated in vivo due to the differing environmental conditions and high variability in gastro-intestinal secretions.

Furthermore, it is known that the secretion of hormones can follow a circadian rhythm. For example cortisol levels are high first thing in the morning and very low around midnight. ACTH and thus cortisol levels begin to rise around 3 am and peak at 7 am gradually falling over the day to a nadir at midnight. A further example of hormones that follow a circadian release pattern is TSH and triiodothyronine (T3). The rise in T3 starts after 2000 h peaks after 2400 h remains high overnight to the time of waking then declines to a nadir around 1500 h. A yet further example is testosterone. A diurnal rhythm is seen for testosterone, which is maximal in the early morning hours and minimal in the evening. The nocturnal testosterone rhythm is related to deep sleep and to rapid eye movement (REM)/non-REM sleep cycles. Peaks in testosterone coincide with the onset of REM sleep. In young men the sleep-related testosterone rise is linked with the appearance of the first REM sleep episode. Increased understanding of the pattern of testosterone production may be of clinical relevance in selecting the appropriate therapeutic regimen and the correct dose required for physiological replacement over the 24-h period for men on long-term testosterone replacement and may aid in the development of male hormonal contraception. Both supraphysiological and subphysiological doses at different time points may have adverse effects reflecting the very widespread distribution of androgen receptors. Supraphysiological doses of testosterone are associated with raised haematocrit, decreased HDL levels and an increase in mean blood pressure whereas inadequate replacement results in anaemia, osteoporosis and loss of libido. In addition testosterone levels have been related to cognitive function specifically spatial awareness and the correct physiological rhythm of testosterone maybe important for optimal cognition.

In middle aged men the secretion of testosterone during the night is reduced when compared to young healthy men suggesting a disruption in the normal rhythm of testosterone release with age, [see Luboshitzky et al Journal of Clinical Endocrinology and Metabolism 88(7): 3160-3166]. It would be desirable to administer steroid hormones in accordance with a circadian rhythm to provide a treatment regime that is closer to the normal physiological secretion of the hormone in hormone replacement therapy.

This disclosure relates to an alternative lipid based formulation for the delivery of steroid hormones, for example testosterone, via the oral lymphatic system and its use in circadian delivery of hormone therapy.

According to an aspect of the invention there is provided a pharmaceutical composition adapted for oral delivery of a steroid comprising:
  a steroid hormone
  a lipid based carrier wherein said carrier includes at least one triglyceride fatty acid wherein the fatty acid is at least 10 carbon atoms in length.

According to an aspect of the invention there is provided a pharmaceutical composition adapted for oral delivery of testosterone or a functional variant of testosterone comprising:
  testosterone, or a functional variant of testosterone,
  a lipid based carrier wherein said carrier includes at least one triglyceride fatty acid wherein the fatty acid is at least 10 carbon atoms in length and at least one agent that enhances the solubility of testosterone or said functional variant in the composition In a preferred embodiment of the invention said steroid hormone is an androgen.

In a preferred embodiment of the invention said androgen is testosterone or dihydrotestosterone.

In an alternative preferred embodiment of the invention said androgen is a functional variant of testosterone.

In a preferred embodiment of the invention said functional variant is selected from the group consisting of: testosterone propionate, testosterone enanthate, testosterone cypionate, testosterone undecanoate, testosterone buciciate, methyltestosterone, fluoxymesterone or mesterolone.

In an alternative preferred embodiment of the invention said steroid hormone is an oestrogen.

Preferably said oestrogen is selected from the group consisting of: oestradiol, estriol and estrone.

In a preferred embodiment of the invention said fatty acid chain length is 10-22 carbon atoms; preferably 14-18 carbon atoms in length.

In a preferred embodiment of the invention the ratio of unsaturated fatty acid to saturated fatty acid is at least or greater than 3.

In a preferred embodiment of the invention said fatty acid is monosaturated.

Preferably said monosaturated fatty acid is at least 30% of the lipid content of the composition.

In an alternative preferred embodiment of the invention said fatty acid is polysaturated.

Preferably said polysaturated fatty acid is at least 30% of the lipid content of the composition.

In a preferred embodiment of the invention said fatty acid is an essential fatty acid.

"Essential fatty acid" means a fatty acid that cannot be naturally synthesized by a human or animal and therefore has to be obtained from the diet. For example essential fatty acids found in plants [e.g. linoleic acid, linolenic acid, oleic acid] and obtained from fish [e.g. docosahexaenoic acid, eicosapentaenoic acid].

In a preferred embodiment of the invention said essential fatty acid is selected from the group consisting of: linoleic acid, linolenic acid, oleic acid, myristoleic acid, palmitoleic acid, arachidonic acid, eicosapentaenoic acid, erucic acid or docohexaenoic acid.

In a preferred embodiment of the invention said essential fatty acid is linoleic acid.

In a preferred embodiment of the invention said essential fatty acid is linolenic acid.

In a preferred embodiment of the invention said essential fatty acid is oleic acid.

In an alternative preferred embodiment of the invention said lipid based carrier is oil.

In a preferred embodiment of the invention said oil is a vegetable oil.

Preferably said vegetable oil is selected from the group consisting of: almond oil, arachis oil, canola oil, cod liver oil, corn oil, cotton seed oil, flaxseed oil, grape seed oil, peanut oil, safflower oil, sesame oil, soybean oil, sunflower oil or walnut oil.

In a preferred embodiment of the invention said oil is sesame oil.

In a preferred embodiment of the invention said composition comprises at least 30%, 31%, 32%, 33%, 34%, 35%, 36%, 37%, 38%, 39% or 40% w/w sesame oil.

In an alternative preferred embodiment of the invention said vegetable oil includes at least one polyalkylene polyol; preferably polyoxyethylated apricot kernel oil polyoxyethylated corn oil or polyethylated hydrogenated coconut.

In an alternative preferred embodiment of the invention said lipid based carrier includes at least one or a combination of fatty acids selected from the group consisting of: caprylic/capric triglycerides (Migyol 810 and 812), caprylic/capric/linoleic triglycerides (Miglyol 818), caprylic/capric/myristic/stearic fatty acid triglycerides (Softisan 378), capylic/capric/succinic fatty acid triglycerides (Miglyol 829), caprylic/capric triglycerides with stearalkonium benonite and propylene carbonate (Migyol Gel T), caprylic/capric triglycerides with stearalkonium hectorite and propylene carbonate (Migyol Gel B)

In a further alternative preferred embodiment of the invention said lipid based carrier includes at least one or a combination of coco-glycerides or coco triglycerides.

Typically, the coco-glycerides or coco triglycerides would comprise 10-18 carbon atoms; for example Softisan 100, 133, 134, 138, 142, 154 which are commercially available.

In a preferred embodiment of the invention said lipid based carrier comprises or consists of myristic acid triglyceride.

In a preferred embodiment of the invention said lipid based carrier comprises or consists of palmitic acid triglyceride.

In a preferred embodiment of the invention said lipid based carrier comprises or consists of stearic acid triglyceride.

In a preferred embodiment of the invention said lipid based carrier comprises a combination of a triglyceride and a polyalkylene polyol.

In a preferred embodiment of the invention said polyalkylene polyol is selected from the group consisting of: polyoxyethylated apricot kernel oil, polyoxyethylated corn oil or polyoxyethylated coconut oil.

In a further preferred embodiment of the invention said lipid based carrier comprises a propylene glycol fatty acid. Preferably said propylene glycol fatty acid is monoester.

Preferably said monoester is propylene glycol monolaurate or propylene glycol monomyristate.

In a preferred embodiment of the invention said monoester is propylene glycol monolaurate.

Preferably, said composition comprises at least 20%, 21%, 22%, 23%, 24%, 25%, 26%, 27%, 28%, 29% or 30% w/w propylene glycol monolaurate.

In an alternative preferred embodiment of the invention said propylene glycol fatty acid is a diester.

Preferably said diester is selected from the group consisting of: dicaprylate/dicaprate, prolylene glycol dicaprylate/dicaprate and propylene glycol dicaprylate/dicaprate.

The compositions of the invention are administered in effective amounts. An "effective amount" is that amount of a composition that alone, or together with further doses, produces the desired response. For example testosterone production rate in men is approximately 3 to 6 mg/day and in women 0.2 to 0.4 mg/day and an effective treatment would deliver this amount of testosterone in to the blood stream in a circadian rhythm with higher levels of testosterone first thing in the morning. For estradiol the daily production rate is approximately 20 to 60 ug per 24 hours and in pubertal girls there is a distinct circadian rhythm with higher levels of estradiol over night peak first thing in the morning.

Such amounts will depend, of course, on the particular condition being treated, the severity of the condition, the individual patient parameters including age, physical condition, size and weight, the duration of the treatment, the nature of concurrent therapy (if any), and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment. It will be understood by those of ordinary skill in the art, however, that a patient may insist upon a lower dose or tolerable dose for medical reasons, psychological reasons or for virtually any other reasons.

In the case of treating hypogonadism the desired response is inhibiting the progression of the disease. This may involve only slowing the progression of the disease temporarily, although more preferably, it involves halting the progression of the disease permanently. Preferably hormone replacement therapy should replace the normal level and rhythm of the hormone. In the case of testosterone that can be assessed by measuring testosterone levels through the 24 hours and in the case of estradiol replacement in measuring 17-beta estradiol over 24 hours. The impact of hormone replacement can also be assessed by measuring the feedback on the pituitary hormones LH and FSH.

The pharmaceutical compositions used in the foregoing methods preferably are non-sterile and contain an effective amount of a steroid hormone for producing the desired response in a unit of weight or volume suitable for oral administration to a patient. The response can, for example, be measured by determining decrease of disease symptoms.

The doses of the steroid hormone administered to a subject can be chosen in accordance with different parameters. Factors include the desired period of treatment. In the event that a response in a subject is insufficient at the initial doses applied, higher doses (or effectively higher doses by a different, more localized delivery route) may be employed to the extent that patient tolerance permits.

When administered, the lipid compositions are applied in pharmaceutically-acceptable amounts and in pharmaceutically-acceptable compositions. The term "pharmaceutically acceptable" means physiologically or toxicologically tolerable. Such preparations may routinely contain salts, buffering agents, preservatives, compatible carriers, and optionally other therapeutic agents. Such agents may be presented or encased within a suitable polymeric capsule dosage form, wherein the capsule can be made from gelatine, hydroxypropylmethyl cellulose (HMPC) or other cellulosic polymer derivatives. To enhance the solubility of the steroid hormone in the lipid composition, typical additives include ethanol, benzyl alcohol, glycerol, propylene glycol, propylene carbonate, diethylene glycol monoethyl ether, cremaphor, polysorbate (Tween 80), or combinations thereof.

In a preferred embodiment of the invention said solubilizing agent is ethanol, and/or benzyl alcohol.

In a preferred embodiment of the invention said composition comprises: testosterone, sesame oil, lauroglycol, ethanol and benzyl alcohol.

In a preferred embodiment of the invention said composition comprises at least 1%, 2%, 3%, 4% or 5% w/w/ethanol.

In a preferred embodiment of the invention said composition comprises at least 5%, 6%, 7%, 8%, 9%, 10%, 11%, 12%, 13%, 14% or 15% w/w benzyl alcohol.

Preferably said composition consists essentially of:
2.5-7.5% w/w testosterone;
at least 40% w/w sesame oil;
at least 30% w/w lauroglycol;
at least 5% w/w ethanol; and
at least 15% w/w benzyl alcohol.

In a preferred embodiment of the invention said composition consists of testosterone, sesame oil, lauroglycol, ethanol and benzyl alcohol as described in table 2.

Compositions may be combined, if desired, with additional pharmaceutically-acceptable carriers to preserve the steroid hormone and protect the lipid based carrier. The term "pharmaceutically-acceptable carrier" as used herein means one or more compatible solid or liquid fillers, diluents or encapsulating substances which are suitable for administration into a human and compatible with a steroid hormone and lipid based carrier. The term "pharmaceutically-acceptable carrier" in this context denotes an organic or inorganic ingredient, natural or synthetic, with which the active ingredient is combined to facilitate the application or protect the active agent. For example these include but are not limited to stabilisers, preservatives, antioxidants, plasticizers to protect the lipid vehicles (or external packaging units thereof) from chemical degradation and/or to preserve the stability of the steroid hormone. Such pharmaceutically acceptable material may include: butylated hydroxyanisole (BHA), butylated hydroxytoluene (BHT), mixed tocopherols, aromatic phenols, lignans, etc.

The components of the pharmaceutical compositions also are capable of being co-mingled with the molecules of the present invention, and with each other, in a manner such that there is no interaction which would substantially impair the desired pharmaceutical efficacy.

The compositions may conveniently be presented in unit dosage form and may be prepared by any of the methods well-known in the art of pharmacy. All methods include the step of bringing the active agent into association with a carrier which constitutes one or more accessory ingredients. In general, the compositions are prepared by uniformly and intimately bringing the active compound into association with a liquid carrier, a finely divided solid carrier, or both, and then, if necessary, shaping the product.

Compositions suitable for oral administration may be presented as discrete units, such as capsules, tablets, lozenges, each containing a predetermined amount of the active compound. Carrier formulation suitable for oral administrations can be found in Remington's Pharmaceutical Sciences, Mack Publishing Co., Easton, Pa.

According to a further aspect of the invention there is provided the use of a composition according to the invention in hormone therapy.

In a preferred embodiment of the invention said hormone therapy is testosterone hormone therapy.

Preferably testosterone therapy is the treatment of male hypogonadism both primary and secondary.

Conditions associated with male hypogonadism include, the treatment of fertility, lack of libido, osteoporosis, increase muscle growth, anaemia, insulin resistance and depression.

In an alternative preferred embodiment of the invention said hormone therapy is oestrogen therapy.

Preferably oestrogen therapy is female hypogonadism.

Conditions associated with female hypogonadism include; hormone replacement therapies in pre-menopausal and postmenopausal women and also to replace hormones lost as a consequence of surgically induce menopause, osteoporosis, vaginal atrophy, amenorrhea and dysmenorrhea.

According to a further aspect of the invention there is provided a method to treat a condition that would benefit from steroid replacement therapy comprising administering an effective amount of the composition according to the invention to a subject in need of hormone replacement wherein the composition is administered in accordance with the circadian secretion of said steroid to provide physiological replacement of said steroid.

Physiological testosterone levels show a distinct circadian rhythm with low levels in the evening and levels rising overnight and peaking in the early hours of the morning. Moreover, oestrogen also shows a circadian pattern of secretion specifically at the onset and during puberty. It would therefore be desirable to provide native 17-beta-oestradiol for oral HRT and especially during puberty this as a circadian therapy.

In a preferred method of the invention said steroid is an androgen.

In a preferred method of the invention said androgen is testosterone or dihydrotestosterone.

In an alternative preferred method of the invention said androgen is a functional variant of testosterone.

In a preferred method of the invention said functional variant is selected from the group consisting of: testosterone propionate, testosterone enanthate, testosterone cypionate, testosterone undecanoate, testosterone buciciate, methyltestosterone, fluoxymesterone or mesterolone.

In a preferred method of the invention said composition is administered prior to sleep; preferably between 20:00 and 24:00.

Preferably said steroid replacement therapy is the treatment of male hypogonadism.

In an alternative preferred method of the invention said steroid is an oestrogen. Preferably said oestrogen is selected from the group consisting of: oestradiol, estriol and estrone.

Preferably said steroid replacement therapy is the treatment of female hypogonadism.

In a preferred method of the invention said composition is administered prior to sleep; preferably between 20:00 and 24:00.

According to a further aspect of the invention there is provided a pharmaceutical composition adapted for oral delivery of a steroid comprising:
  a steroid,
  a lipid based carrier wherein said carrier includes at least one triglyceride fatty acid wherein the fatty acid is at least 10 carbon atoms in length and at least one agent that enhances the solubility of the steroid in the composition In a preferred embodiment of the invention said steroid hormone is an oestrogen.

Preferably, said oestrogen is selected from the group consisting of: oestradiol, estriol and estrone.

Throughout the description and claims of this specification, the words "comprise" and "contain" and variations of the words, for example "comprising" and "comprises", means "including but not limited to", and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

An embodiment of the invention will now be described by example only and with reference to the following Figures and tables:

Figure 3:
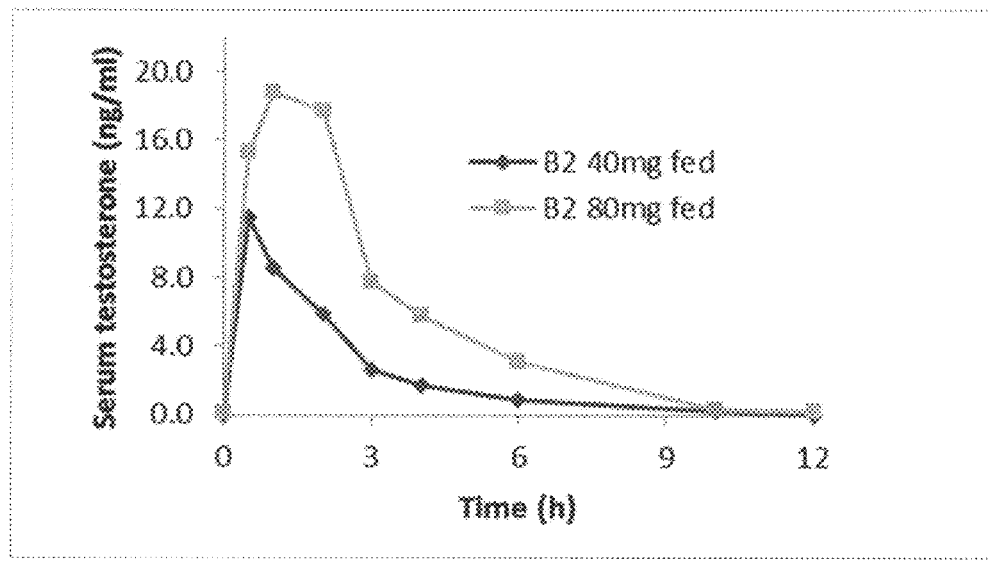
Figure 4:
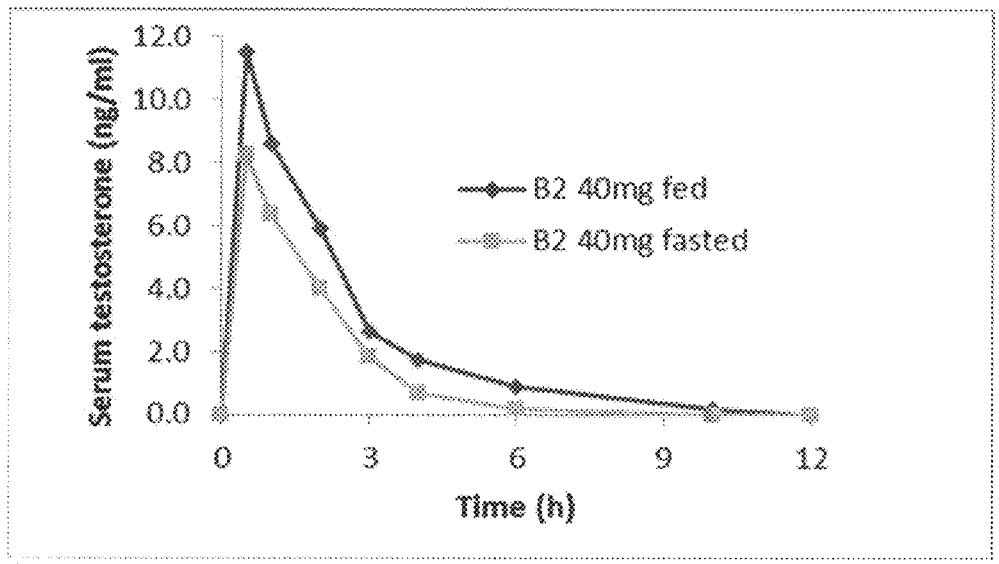

FIG. 3: illustrates pharmacokinetic profiles for testosterone lipidic formulation B2 dosed at 40 mg and 80 mg to female beagle dogs under fed state; and FIG. 4: illustrates pharmacokinetic profiles for testosterone lipidic formulation B2 dosed at 40 mg to female beagle dogs under fasted and fed states.

MATERIALS AND METHODS

The lipid system for use the delivery of testosterone may be selected from natural edible oils, specific distilled fractions thereof or synthetically modified derivatives. Such systems include:

A Edible oils derived from vegetable or animal sources with triglycerides containing fatty acids with (predominantly) chain lengths in excess of 10-carbon units i.e., almond oil, arachis (ground-nut) oil, canola oil, cod liver oil, corn (maize) oil, cotton seed oil, flaxseed oil, grape seed oil, peanut oil, safflower oil sesame oil, soybean oil, sunflower oil and walnut oil, see Table 1.

TABLE 1

| Excipient | Percentage in formulation % (w/w) | | | | | | |
|---|---|---|---|---|---|---|---|
| | A | B | C | D | E | F | G |
| Testosterone | 10.93 | 10.91 | 4.62 | 4.60 | 5.72 | 5.79 | 24.97 |
| Ethanol | 5.00 | 5.00 | 15.05 | 15.01 | 4.92 | 4.98 | — |
| Transcutol | — | — | 5.04 | 5.03 | 4.97 | 5.03 | — |
| Benzyl Alcohol | 15.03 | 15.01 | — | — | 9.88 | 9.99 | — |
| Lauroglycol | 30.00 | 29.96 | 30.10 | 30.01 | 29.53 | 29.88 | — |
| Corn Oil | 39.04 | — | 45.19 | — | 45.00 | — | — |
| Sesame Oil | — | 39.12 | — | 45.36 | — | 44.34 | — |
| Gelucire 44/14 | — | — | — | — | — | — | 75.03 |
| Typical dose of testosterone in size 00 capsule (mg) | 80 mg | 80 mg | 35 mg | 35 mg | 40 mg | 40 mg | 20 mg |

B Distilled fractions of mid to long chain triglycerides such as caprylic/capric triglycerides (Migyol 810 and 812), caprylic/Capric/Linoleic triglycerides (Miglyol 818), Caprylic/Capric/Myristic/Stearic triglycerides (Softisan 378), Capylic/Capric/Succinic triglycerides (Miglyol 829), Caprylic/Capric triglycerides (and) stearalkonium benonite (and) propylene carbonate (Migyol Gel T), Caprylic/Capric triglycerides (and) stearalkonium hectorite (and) propylene carbonate (Migyol Gel B), see Table 2.

TABLE 2

| Excipient | Supplier | Percentage in system (w/w) | | | |
|---|---|---|---|---|---|
| | | B1 (80 mg Testosterone) | B2 (40 mg Testosterone) | B3 (20 mg Testosterone) | B4 (10 mg Testosterone) |
| Testosterone | Fagron UK Ltd | 10.91 | 5.46 | 2.73 | 1.37 |
| Ethanol | Fisher Scientific | 5.00 | 5.30 | 5.46 | 5.54 |
| Benzyl Alcohol | Fisher Scientific | 15.01 | 15.93 | 16.39 | 16.62 |
| Lauroglycol | Gattefosse | 29.96 | 31.80 | 32.72 | 33.16 |
| Sesame Oil | Statfold oils Ltd | 39.12 | 41.51 | 42.70 | 43.31 |
| Total | | 100.00 | 100.00 | 100.00 | 100.00 |
| Typical testosterone dose in size 00 capsule | | 80.00 mg | 40.00 mg | 20.00 mg | 10.00 mg |

C Distilled fractions of mid to long chain of hydrogenated coco-glycerides-triglycerides of C10-C18 fatty acids (Softisan 100, 133, 134, 138, 142, 154), see Table 3.

TABLE 3

| Excipient | | Percentage in system (w/w) | | |
|---|---|---|---|---|
| | | D1 (34 mg Testosterone) | D2 (17 mg Testosterone) | D3 (8.5 mg Testosterone) |
| Testosterone | Fagron UK Ltd | 4.60 | 2.30 | 1.15 |
| Ethanol | Fisher Scientific | 15.01 | 15.37 | 15.55 |
| Transcutol | Gattefosse | 5.03 | 5.15 | 5.21 |
| Lauroglycol | Gattefosse | 30.00 | 30.73 | 31.09 |
| Sesame Oil | Statfold oils Ltd | 45.36 | 46.45 | 47.00 |
| Total | | 100.00 | 100.00 | 100.00 |
| Typical dose of testosterone in size 00 capsule | | 34.00 mg | 17.00 mg | 8.50 mg |

D Distilled fractions of individual fatty acids—triglyceride of myristic acid (Trimyristin Dynasan 1140, triglyceride of palmitic acid (Tripalmintin Dynasan 116) and triglycerides of stearic acid (Tristearin Dynasan 118), see Table 4.

TABLE 4

| Oral dose administration occasion | Formulation identification | Dose/ capsule | No. of capsules per dog | Overall Testosterone dose | Fasted or fed state |
|---|---|---|---|---|---|
| 1 | B2 | 40 mg | 1 | 40 mg | Fasted |
| 2 | B2 | 40 mg | 1 | 40 mg | Fed |
| 3 | B2 | 40 mg | 2 | 80 mg | Fed |
| 4 | B3 | 20 mg | 2 | 40 mg | Fed |
| 6 | Control | 40 mg | 1 | 40 mg | Fed |

E Transesterified products of natural or hydrogenated vegetable oil triglyceride and a polyalkylene polyol—polyoxyethylated apricot kernel oil (Labrafil M1944CS), polyoxyethylated corn oil (Labrafil M2125CS) and Polyethylated hydrogenated coconut (Gelucire 37/06), see Table 5.

TABLE 5

Summary of the dispersion
stability data for lipidic formulations for testosterone

| | Percentage in system (w/w) | | |
|---|---|---|---|
| Form-ulation | Dispersion stability in gastric environment | Dispersion stability in intestinal environment | Physical stability after 2-weeks at RT and 50° C. |
| B1 | Capsule dissolves within 1 minute. Solution stable up to 10 minutes | Stable up to 10 minutes | No precipitation, discolouration or leakage |
| B2 | Capsule dissolves within 1 minute. Solution stable up to 1-hour | Stable up to 1-hour | No precipitation, discolouration or leakage |
| B3 | Capsule dissolves within 1 minute. Solution stable beyond 1-hour | Stable beyond 1-hour | No precipitation, discolouration or leakage |
| D1 | Capsule dissolves within 1 minute. Solution stable up to 10 minutes | Stable up to 30 minutes | No precipitation, discolouration or leakage |
| D2 | Capsule dissolves within 1 minute. Solution stable up to 1-hour | Stable up to 30 minutes | No precipitation, discolouration or leakage |
| D3 | Capsule dissolves within 1 minute. Solution stable up to 1-hour | Stable up to 1-hour | No precipitation, discolouration or leakage |

F Propylene glycol mono- and/or di-esters of fatty acids—propylene glycol monolaurate (Lauroglycol), propylene glycol monomyristate (Mipryl) propylene glycol dicaprylate/dicaprate (Capex 200), prolylene glycol dicaprylate/dicaprate (Miglyol 840) and propylene glycol dicaprylate/dicaprate (Neobee M-20), see Table 6.

TABLE 6

Summary of pharmacokinetic parameters for the
lipidic formulations of testosterone in female
beagle dogs analysed using Kenetica 5.0 (Thermo Fisher)

| | Pharmacokinetic parameters | | |
|---|---|---|---|
| Formulation | Concentration of maximal serum of testosterone (Cmax) – ng/ml | Time to achieve maximum serum concentration for testosterone (Tmax) – h | Area under the curve (AUC) – ng/ml · h |
| B2 - 40 mg under fasted state | 8.3 | 0.5 | 15.7 |
| B2 - 40 mg under fed state | 11.5 | 0.5 | 26.4 |
| B2 - 80 mg under fed state | 18.8 | 1.0 | 64.1 |
| B3 - 40 mg under fed state | 10 | 0.5 | 44.4 |
| Control - 40 mg testosterone suspension in sesame oil | 8.5 | 1.0 | 23.7 |

Formulation Systems

The formulation systems as detailed in Table 1 all show significant solubilisation capacity for testosterone (>50 mg/[1]) which is at least 100-fold higher than that achievable in aqueous media (<0.3 mg/g[1]) and at least 5-fold higher than that achievable in single component lipidic vehicles alone (max.<10 mg/g).

[1]N.B: For aqueous systems 1 g=1 mL; for oil systems 1 g=>1 mL

Tables 2 and 3 show lipidic formulations for testosterone based on formulation system B and D respectively (see Table 1) wherein the overall concentration of testosterone can be changed in order to meet therapeutic requirements and for optimising the formulation dispersion stability along the gastrointestinal tract.

Preparation of Lipidic Formulations for Testosterone

Formulation systems detailed in Tables 1-3 were prepared in accordance with the methods described below:

a. The liquid excipients, in the weight ratio specified for each of the formulations, were mixed in a suitable vessel to form a homogeneous vehicle b. Testosterone, in the specified quantity, was added to the homogeneous vehicle with continuous stirring and application of gentle heat as appropriate, to ensure complete dissolution c. Aliquot of the testosterone solution was filled into the appropriate size capsule (nominally capsule size 00) to provide the appropriate dose strength d. The capsule lid was seal to the capsule body with a gelatin solution of appropriate viscosity to produce a tight (leak-free) seal Dispersion Stability in Gastrointestinal Environment The dispersion stability of lipidic formulations of testosterone as described in Tables 2-4 were evaluated under simulated gastric (pH1) and intestinal (pH6.8) conditions. Samples were evaluated by placing the testosterone formulation (filled in gelatin capsule) in 250 ml of media maintained at 37° C. in a Caleva dissolution bath. Gentle agitation was provided using paddle apparatus at 50 rpm. The dispersibility was monitored visually for precipitation and the time formulations remained in solution. Solution systems were monitored at 15, 30 and 60 minutes, if any precipitation occurred further testing was stopped. If no change was observed the test was continued and monitored every hour up to 7 hours, and left overnight for 24 hours.

Stability Study

The physical stability of lipidic formulations of testosterone as described in Tables 2-3, were evaluated at room temperature (20-25° C.) and under accelerated temperature condition (50° C.) over a period of 2-weeks. Lipidic formulations of testosterone were filled into size 00 gelatin capsules and placed on stability at each of the specified storage conditions. The capsules were stored upright (and horizontally) in glass vials. All samples were monitored daily over a period of two weeks for discoloration, precipitation, separation and leakage (from capsules).

In Vivo Study

The absorption behavior of lipidic formulations B2 and B3 was evaluated in female beagle dogs in 6 phases with a washout period of at least 6 days between administrations. All formulations were dosed to the animals under fed conditions and one formulation (B2) was also dosed under fasted condition. A control formulation comprising a suspension of testosterone in sesame oil was included as a control. Details of the test articles and dosing sequence are shown in Table 4.

Each of the test formulations were administered to a group of 4 beagle dogs, aged approximately 1-2 years, weighing approximately 6-10 kg. During the pre-trial holding and study periods, the animals were housed in caging appropriate to the species. Temperature and relative humidity were controlled during the acclimatization and study periods.

A daily allowance of 400 g of a standard laboratory diet of known formulation (Harlan Teklad Global Diet Coded 2021) was made available to each dog. For FED experiments dogs were given a meal 30 minutes before dosing and for the FASTED experiment dogs were fasted overnight and food given 2 hours post administration.

Blood samples were collected up to 24 h post-dose in 4 female dogs following oral administration (6 phases). Blood samples (ca 0.5 mL) were removed from the jugular vein into uniquely-labelled tubes with clot activator gel (BD Vacutainer® gold top), at the following target times: pre-dose, 0.5, 1, 2, 3, 4, 6, 10, 12 and 24 h post dosing.

Analysis of testosterone in the blood samples was conducted using conventional solid phase extraction (precipitation from methanol) and testing via liquid chromatography separation and detection via mass spectrometry. The pharmacokinetic parameters were derived by non-compartmental analysis using Kenetica 5.0 (Thermo Fisher).

EXAMPLES

A summary of the key in vitro formulation performance dataset is provided in Table 5. All non-formulation systems showed rapid dissolution of the gelatin capsule to release the content into the gastric environment. Following release of the testosterone solution, all formulations showed a loading concentration dependent dispersion stability profile. At very high testosterone loading concentration (formulations B1, >10 mg/g) stability was maintained up to 10-minutes before evidence of fine (and limited) precipitation. At lower concentrations, formulation systems (B2, B3 and B4) were stable up to and beyond 1-hour sufficient for absorption to occur from the gastrointestinal tract.

All tested formulations were found to be physically stable under ambient and accelerated testing conditions over a 2-week test period. No precipitation, discoloration or leakage from the capsule was observed.

Figure 1:
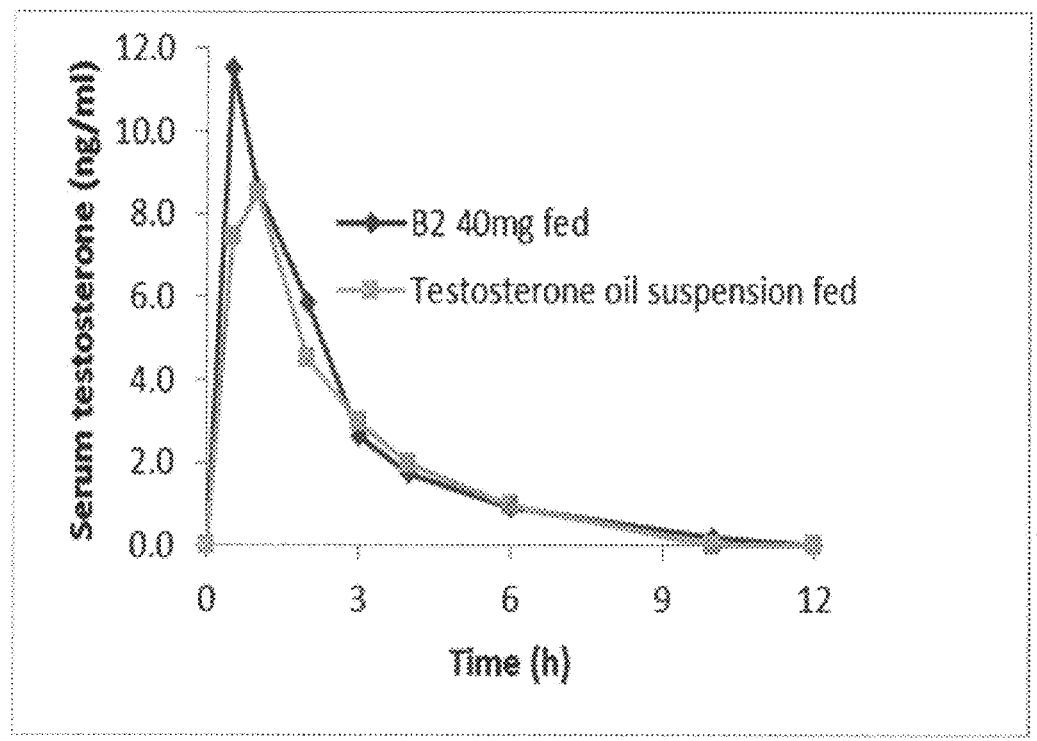
FIG. 1 illustrates pharmacokinetic profiles for testosterone lipidic formulation B2 and testosterone control formulation dosed at 40 mg to female beagle dogs under fed state.
Figure 2:
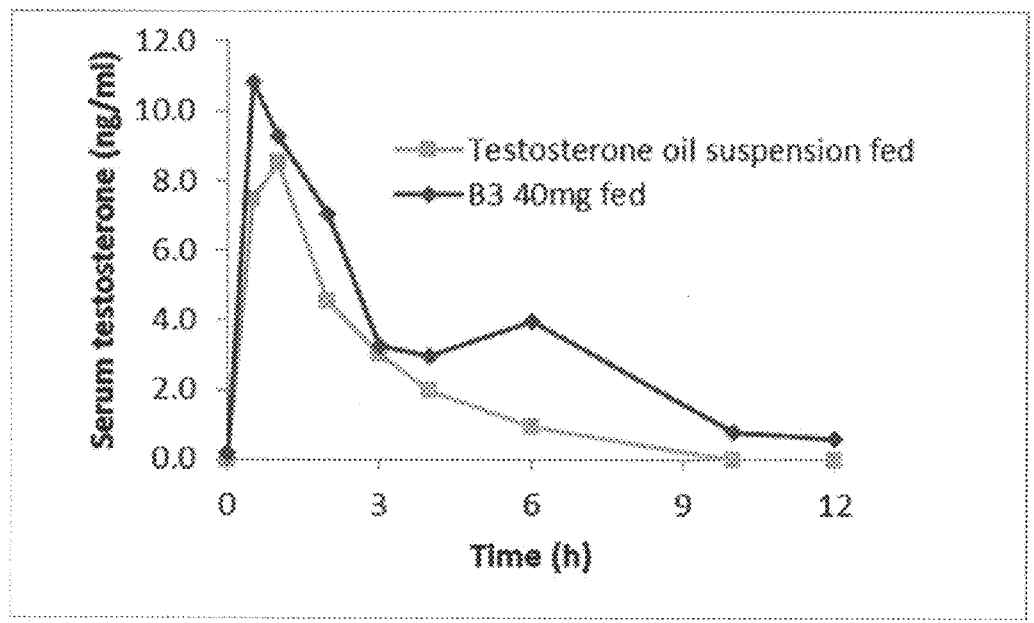
FIG. 2 illustrates pharmacokinetic profiles for testosterone lipidic formulation B3 and testosterone control formulation dosed at 40 mg to female beagle dogs under fed state.

The pharmacokinetic profiles for representative lipidic formulations of testosterone in female beagle dogs are shown in FIGS. 1-4. All lipidic formulations were profiled against a control formulation containing testosterone suspension in sesame oil. FIGS. 1 and 2 show the pharmacokinetic profiles for the lipidic formulations versus the control formulation, all dosed under fed state. The overall extent of absorption, characterised by the maximal serum concentration for testosterone (Cmax) and the area under the curve (AUC) was significantly higher (11-77%) for the lipidic formulations (B2 and B3) than for the control formulation at an equivalent dose. Furthermore, FIG. 3 shows that by increasing the total administered dose from 40 mg to 80 mg, the level of exposure (as reflected by the AUC) increased disproportionately with dose to over 3-fold (Table 6). FIG. 4 shows that dosing of formulation B2 to the animals under fasted state resulted in a reduction in AUC of only c. 30%, which is significantly less than that observed for testosterone related oral formulations wherein the reduction in bioavailability under fasted state can exceed 20-fold[1]

[1]Schnabel et al., The effect of food composition on serum testosterone levels after oral administration of Andriol® Testocaps® Clin Endocrinol, 2007 Apr. 1; 66(4): 579-585

The invention claimed is:

1. A pharmaceutical composition adapted for oral delivery of an effective amount of an effective amount of native testosterone consisting of:
   2.5-7.5% w/w native testosterone;
   at least 40% w/w sesame oil;
   at least 30% w/w lauroglycol;
   at least 5% w/w ethanol;
   at least 15% w/w benzyl alcohol; and
   a pharmaceutically acceptable carrier wherein the combination of ethanol and benzyl alcohol increases the solubility and bioavailability of native testosterone when administered to a subject.

2. The composition according to claim 1 wherein the effective amount of native testosterone is 40 mg.

3. The composition according to claim 1 wherein the effective amount of native testosterone is 20 mg.

4. A method to treat male hypogonadism, comprising:
   administering an effective amount of the composition of claim 1 to a male subject having hypogonadism, wherein the composition is administered in accordance with the circadian secretion of testosterone to provide physiological replacement of testosterone, thereby treating the male hypogonadism.

5. The method according to claim 4, wherein the composition is administered prior to sleep between 20:00 hours and 24:00 hours.

6. The composition according to claim 1, consisting of 5.46% w/w native testosterone, 5.3% w/w ethanol, 15.93% w/w benzyl alcohol, 31.80% w/w lauroglycol and 41.51% w/w sesame oil.

7. The composition according to claim 1, consisting of 2.73% w/w native testosterone, 5.46% w/w ethanol, 16.39% w/w benzyl alcohol, 32.72% w/w lauroglycol and 42.7% w/w sesame oil.

8. The composition according to claim 1 wherein said composition is contained in a capsule.

9. The method according to claim 4, wherein the male hypogonadism is primary male hypogonadism.

10. The method according to claim 4, wherein the male hypogonadism is secondary male hypogonadism.

* * * * *